(12) United States Patent
Foguet et al.

(10) Patent No.: US 7,635,691 B2
(45) Date of Patent: *Dec. 22, 2009

(54) USE OF CDP-CHOLINE FOR THE PROPHYLACTIC TREATMENT OF CEREBRAL ISCHEMIA

(75) Inventors: Rafael Foguet, Barcelona (ES); Jorge Ramentol, Barcelona (ES); Isidro J. Ferrer, Barcelona (ES); Rafael Lozano, Barcelona (ES); Julio J. Secades, Barcelona (ES); Manuel M. Raga, Barcelona (ES); Josep M. Castello, Barcelona (ES); José A. Ortiz, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 971 days.

This patent is subject to a terminal disclaimer.

(21) Appl. No.: 11/133,251

(22) Filed: May 20, 2005

(65) Prior Publication Data

US 2005/0222077 A1    Oct. 6, 2005

Related U.S. Application Data

(62) Division of application No. 10/221,581, filed as application No. PCT/EP01/02825 on Mar. 13, 2001, now Pat. No. 6,930,096.

(30) Foreign Application Priority Data

Mar. 14, 2000    (ES) ................................ 200000610

(51) Int. Cl.
*A61K 31/70*    (2006.01)

(52) U.S. Cl. ........................................................ 514/49
(58) Field of Classification Search .................... 514/49
See application file for complete search history.

(56) References Cited

U.S. PATENT DOCUMENTS 5,872,108 A    2/1999   Fisher et al.
6,930,096 B2 *  8/2005   Foguet et al. .................. 514/49

FOREIGN PATENT DOCUMENTS

CN    1 122 241 A    5/1996
JP    63-313594 A    12/1988

OTHER PUBLICATIONS

Bricourt et al., *Agressolgie*. vol. 31, No. 7, pp. 457-463 (1990).
Alvarez et al., *Clinical Pharmacology*, vol. 21, No. 8, pp. 535-540 (1999).
Trovarelli et al., *Neurochemical Research*, vol. 6, No. 8, pp. 821-833 (1981).
Tornos et al., *Arzneimittel-Forschung*, vol. 33, No. 7A, pp. 1022-1024 (1983).
Tazaki et al., *Stroke, American Heart Association*, vol. 19, No. 2, pp. 211-216 (1988).
Bruhwyler et al., *Current Therapeutic Research*, vol. 58, No. 5, pp. 309-316 (1997).
Merck Manual of Diagnosis and Therapy, 14th ed., Berkow et al. (eds.), published 1982 by Merck & Co., Inc. pp. 1327-1329.

* cited by examiner

*Primary Examiner*—Raymond J Henley, III
(74) *Attorney, Agent, or Firm*—Birch, Stewart, Kolasch & Birch, LLP

(57) ABSTRACT

The invention describes a prophylactic treatment of cerebral ischemia with CDP-Choline in patients who have undergone major surgery or are at risk of suffering an acute ischemic event.

12 Claims, 5 Drawing Sheets

USE OF CDP-CHOLINE FOR THE PROPHYLACTIC TREATMENT OF CEREBRAL ISCHEMIA

CROSS-REFERENCE TO RELATED APPLICATIONS

This application is a 37 C.F.R. 1.53(b) divisional of and claims priority to U.S. application Ser. No. 10/221,581, filed on Sep. 13, 2002, now U.S. Pat. No. 6,930,096 B2. Application Ser. No. 10/221,581 is the National Phase under 35 U.S.C. 371 of PCT International Application No. PCT/EP01/02825, which has an International filing date of Mar. 13, 2001, which designated the United States of America. PCT/EP01/02825 also claims priority to Spanish Patent Application No. P200000610, filed on Mar. 14, 2000.

DESCRIPTION

The present invention relates to the use of CDP-Choline for the prophylactic treatment of cerebral ischemia.

There are several factors involved in the occurrence and extent of cerebral ischemic disorders secondary to ischemia. These factors include: energy failure and loss of neurotransmitter homeostasis and cations; induction and casual expression of early genes, as well as mobilization of cytokines, that change blood-brain barrier function and participate in leukocyte infiltration; rapid cell death in infarct central zones and delayed death—frequently associated to apoptosis—in peripheral or penumbra areas; and induction or expression of trophic factors and their receptors that promote reparative plastic phenomena and angiogenesis.

Knowledge of cellular death mechanisms after an ischemic event is an underlying aspect, since their control make possible the external therapeutic capacity. The genetic control of programmed cell death has been mainly investigated in the nematode *Caenorhabditis elegans* and is related to genes ced-3, ced-4 and ced-9. Caspases, a type of cysteine-dependent mammalian proteases, correspond to some counterparts of ced-3 gene product and are crucial to the development of apoptosis. Caspases are differentially involved in several cellular death models and act on different underlying substrates for cell survival resulting in their disintegration. Caspases 1, 2, 3, 6 and 8 are related to different central nervous system diseases. T. E. Andreoli (*Am. J. Med.*, 107, 488-506, 1999) and B. C. Albensi (*Drug News Perspect.*, 12(8), 453-457, 1999) reviewed thoroughly the phenomenon of apoptosis and the role of caspases.

There are at present few literature data on the expression of caspases after damage induced by transient global ischemia or focal ischemia. Current studies have shown a variable expression for each caspase depending on involved time and cell types. Applicants have found that caspases participate in the ischemic episode—both in human brain and in rat focal ischemia model—and that the expression of caspases is evidenced to be particularly prominent in the penumbra area within the first days of infarction.

CDP-Choline (cytidine-diphosphate-choline, Citicoline) is a key precursor for the synthesis of membrane phosphatidyl choline. In experimental models, the exogenous administration of CDP-Choline reduces the breakdown of cell membranes by inducing an increase of phosphatidyl choline synthesis and a decrease of free fatty acid levels. Treatment with CDP-choline proved to be beneficial in several ischemia or hypoxia animal models. Antiapoptic, neuroprotective and antiamnesic effects of CDP-Choline have been experimentally investigated in rats by X. A. Alvarez et al. (*Methods and Findings in Experimental and Clinical Pharmacology*, 21(8), 535-540, 1999). The neuroprotective mechanism of CDP-choline is not known to the full extent. At present, this effect is believed to be related to a reduction of free fatty acids, production of free radicals, stabilization of nerve cell membranes, decrease of glutamate-induced toxicity and increase of nerve cell survival. Whether the beneficial effect of CDP-Choline in eschemic episodes may be related to the reduction of cell death by apoptosis in post focal ischemia penumbra area has not yet been elucidated.

Surprisingly it was found that the administration of CDP-Choline before a cerebral ischemic episode produces a larger beneficial effect in preventing severity of sequelae than if CDP-Choline is administered after the onset of sequelae.

The present invention relates to the use of CDP-Choline or of a pharmaceutically acceptable salt thereof for the manufacture of a medicament for the prophylactic treatment of cerebral ischemia.

Prophylactic treatment means that CDP-Choline or a pharmaceutically acceptable salt thereof is administered before the eventual onset of an ischemic episode. In the event an ischemic episode occurs, it is preferred to continue the treatment. The mode of treatment may then be adapted to the patient's needs.

Viewed from another aspect, the invention relates to neuroprotective treatment. Neuroprotection means protecting brain tissue from damage, in particular from cerebral infarction.

According to another aspect, the present invention relates to the use of CDP-Choline or of a pharmaceutically acceptable salt thereof for preventing the extent of the brain tissue damage.

According to a specific embodiment, the present invention relates to the above use in which brain tissue damage and in particular cerebral infarction is associated with cerebral ischemia.

Cerebral ischemia comprises cerebral ischemic events. An ischemic event may be defined as the reduction of blood supply to a tissue. Cerebral ischemia may be caused by reduction or even interruption of blood supply from the artery feeding the brain.

CDP-Choline possesses an inhibitory effect on caspase chain activation and reduces nerve cell apoptosis in the penumbra area.

Thus, viewed from another aspect, the present invention relates to the use of CDP-Choline or of a pharmaceutically acceptable salt thereof for inhibiting caspase chain activation. Since this effect was higher in pretreated subjects, it is concluded that CDP-Choline exerts a prophylactic neuroprotective effect in cerebral ischemic events. In short, the fact that CDP-Choline is more effective when administered before ischemia suggests a preventive action on the severity of ischemic complications. Finally, the prophylactic method of the present invention is advantageously more effective than conventional treatment a posteriori.

The use according to the present invention includes a method for the prophylactic treatment of cerebral ischemia comprising administering to a subject in need thereof of an effective amount of CDP-Choline or of a pharmaceutically acceptable salt thereof.

CDP-Choline or its pharmaceutically acceptable salts or mixtures thereof, may be administered or optionally co-administered sequentially or simultaneously with further therapeutic agents, in pharmaceutically acceptable form, e.g., conveniently mixed with pharmaceutical carriers and/or excipients, to a subject in need thereof, usually human patients, in an effective amount, preferably at daily doses ranging from 0.5 to 4 g in free CDP-Choline, more preferably from 1 to 2 g in CDP-Choline, both orally and parentally, depending on the patient's state.

Pharmaceutically acceptable salts of CDP-Choline include its base addition salts, in particular alkaline or alkaline earth salts, such as its sodium, potassium, calcium and magnesium salts or its acid addition salts with a mineral or organic acid, such as hydrochloric acid, hydrobromic acid, sulphuric acid, acetic acid, trifluoroacetic acid, citric acid, lactic acid, acid, malonic acid, tartaric acid, acrylic acid, metacrylic acid, malic acid, maleic acid, fumaric acid, benzoic acid, salicylic acid, cinnamic acid, methane sulphonic acid, benzenesulphonic acid, p-toluensulphonic acid and nicotinic acid.

CDP-Choline or its salts may be used in anhydrous or solvated, in particular hydrated, form.

Administration may be orally in the form of tablet, capsule, powder, granule, cachet, lozenge, solution, suspension, emulsion, syrup, gel and the like; or parentally in the form of solution, suspension, emulsion or the like for intravenous or intramuscular injection.

Subjects in need of the treatment according to the present invention are specially:

Patients subjected to major surgery, i.e., patients who will undergo, are undergoing and in particular have undergone surgical operations in which hemorrhages, vascular manipulation or induced and maintained hypotension (neurosurgery, cardiovascular surgery, organ transplants, implant of orthopedic prosthesis, etc.) are likely to and in particular have occurred. In these cases, it is preferred to start treatment 24-48 hours before surgical operation at effective oral doses of e.g., 1-2 g/day. Drug administration is continued during surgical operation at effective doses of e.g., 1-2 g by the intravenous route at the time of inducing anesthesia, and then for 1 week at effective doses of e.g., 1-2 g/day by the oral or intravenous route depending on the patient's state.

Patients at high risk of suffering an acute ischemic event such as stroke due to several known risk factors, such as a history of previous transient ischemic episodes, arterial hypertension, hypercholesterolemia, smoking, auricular fibrillation or other embolic heart disease. In this case, patients should be treated with effective doses of e.g. 1-2 g/day by the oral route even after having suffered a hypothetical stroke.

EXAMPLES

Formulations of the active ingredient, suitable for application of the method of the present invention, are illustrated in the following examples. Those skilled in the art will be able to make any change provided the specific embodiment of the invention is not modified and, therefore, the invention is not limited to the specific details of these examples.

Example 1

500 mg Tablets

| | |
|---|---|
| CDP-Choline, sodium salt | 522.5 mg |
| Talc | 30.9 mg |
| Magnesium stearate | 3.0 mg |
| Silicon dioxide | 2.5 mg |
| Croscarmellose sodium | 20.0 mg |

-continued

| | |
|---|---|
| Corn starch | 20.0 mg |
| Microcrystalline cellulose s.q. | 780.0 mg |

Example 2

25% Oral Solution

| | |
|---|---|
| CDP-Choline, sodium salt | 26.12 g |
| 70% Sorbitol | 20.00 g |
| Methyl p-hydroxybenzoate | 0.16 g |
| Propyl p-hydroxybenzoate | 0.04 g |
| Disodium citrate | 0.60 g |
| Saccharin sodium | 0.02 g |
| Strawberry essence | 0.04 g |
| Red Punzo 4R | 0.50 g |
| Anhydrous citric acid | 0.05 g |
| Purified water s.q. | 100.00 ml |

Example 3

Solution for Intravenous Injection

| | |
|---|---|
| CDP-Choline, sodium salt | 522.50 mg |
| Hydrochloric acid, pH 6.0-6.5, q.s. | |
| Water q.s. | 4.00 ml |

Example 4

Neuroprotective Action

The effect of CDP-Choline on deferred nerve cell death (apoptosis) has been assessed in a model of cortical cerebral ischemia in the rat in accordance with the following experimental protocol:

1) Animals:

All cerebral infarction tests were performed in male Sprague-Dawley rats weighing 220-270 g. Animals were housed, with free access to food and water, in temperature- and humidity-controlled rooms with a 12/12 h light-dark cycle.

2) Model of Middle Cerebral Artery Occlusion:

Cerebral ischemia was induced by a permanent proximal occlusion of the middle cerebral artery using electrocoagulation. Under deep anesthesia, the rat head was clipped and an incision was made between the left ear and the left eye. Then, the cranium was exposed by sectioning the temporal muscle. Craniotomy was performed using a 1-2 mm drill behind the scaly fissure. The dura mater was drilled in order to expose the middle cerebral artery arm which was permanently coagulated.

3) Treatments:

Rats were randomly divided into three groups:

(a) After 30 minutes of ischemia, the animals in this group were treated with CDP-Choline (500 mg/kg) in 0.9% sterile physiologic saline (0.1 ml) administered intraperitoneally. This group is depicted in FIGS. 1 through 5 as "After."

(b) Since 24 hours before ischemia and after 30 minutes of ischemia, the animals in this group received the same treatment as in group (a). This group is depicted in FIGS. 1 through 5 as "Before."

(c) The animals in this group were used as control. After ischemia, they were treated with 0.9% physiologic saline vehicle (0.1 ml) administered intraperitoneally. This group is depicted in FIGS. 1 through 5 as "Control."

4) Preparation of Samples for Morphological Studies.

Fragmented DNA labeling and caspase immunohistochemistry:

The animals were allowed to recover at different times (30 min and 1, 4, 8, 12, 24 and 48 hours) before terminal anesthesia with ethyl ether. Then, the brains were immediately perfused with PBS at 4° C., by using a cannula inserted into the heart (left ventricle), followed by 4% paraformaldehyde. The brains were quickly removed and fixed by immersion in the same fixative for 24 h at 4° C. After cryoprotection using 30% saccharose, the brains were frozen in isopentane cooled with liquid nitrogen and subsequently preserved at −70° C. Using a cryostat, the brains were sectioned into 50 µm slices. The brain slices were preserved at −70° C. using a cryoprotector. These sections were used afterwards as samples for immunohistochemistry, morphology and in situ labeling of apoptotic cells. The morphology of infarction was studied in sequential sections including the start and end of infarction by using hematoxylin and eosin stain and Nissl's stain (cresyl violet). The apoptotic cells were labeled by variants of fragmented DNA in situ labeling. Immunohistochemistry of caspase expression was performed using the avidin-biotin-peroxidase method with specific primary antibodies for caspases 1, 2, 3, 6 and 8 obtained from Santa Cruz Biotechnology.

5) Gel Electrophoresis and Western Blot Analysis:

The preparation of samples concerning groups and times is similar to that of item 4). The animals, which were deeply anesthetized, were decapitated and the brains were freshly removed. In each case, the following regions were dissected: a) gray substance of infarct area; b) white substance of infarct area; c) gray substance of penumbra area; and d) white substance of penumbra area. In each case, samples were obtained from ipsilateral and contralateral side. These samples were subsequently used for Western blot analysis of anticaspase antibodies and antibodies against different caspase substrates in order to know their possible degradation after ischemic damage.

6) Results:

For assessment of the effect of treatment, the expression of caspases 1, 2, 3, 6 and 8, as markers of apoptosis process, was measured 12 hours after infarction induction, whose results are shown in FIGS. 1, 2, 3, 4, and 5, respectively. Applicants have observed that there are significant differences between treated and control animals as for expression of these markers. In addition, and what is more important, these differences are more significant in the animals receiving treatment before ischemia than in the animals receiving treatment after ischemia. All these experiments make evident that CDP-Choline when administered before and after infarction induction decreases caspase level more significantly than when administered only after infarction induction.

Figure 1:
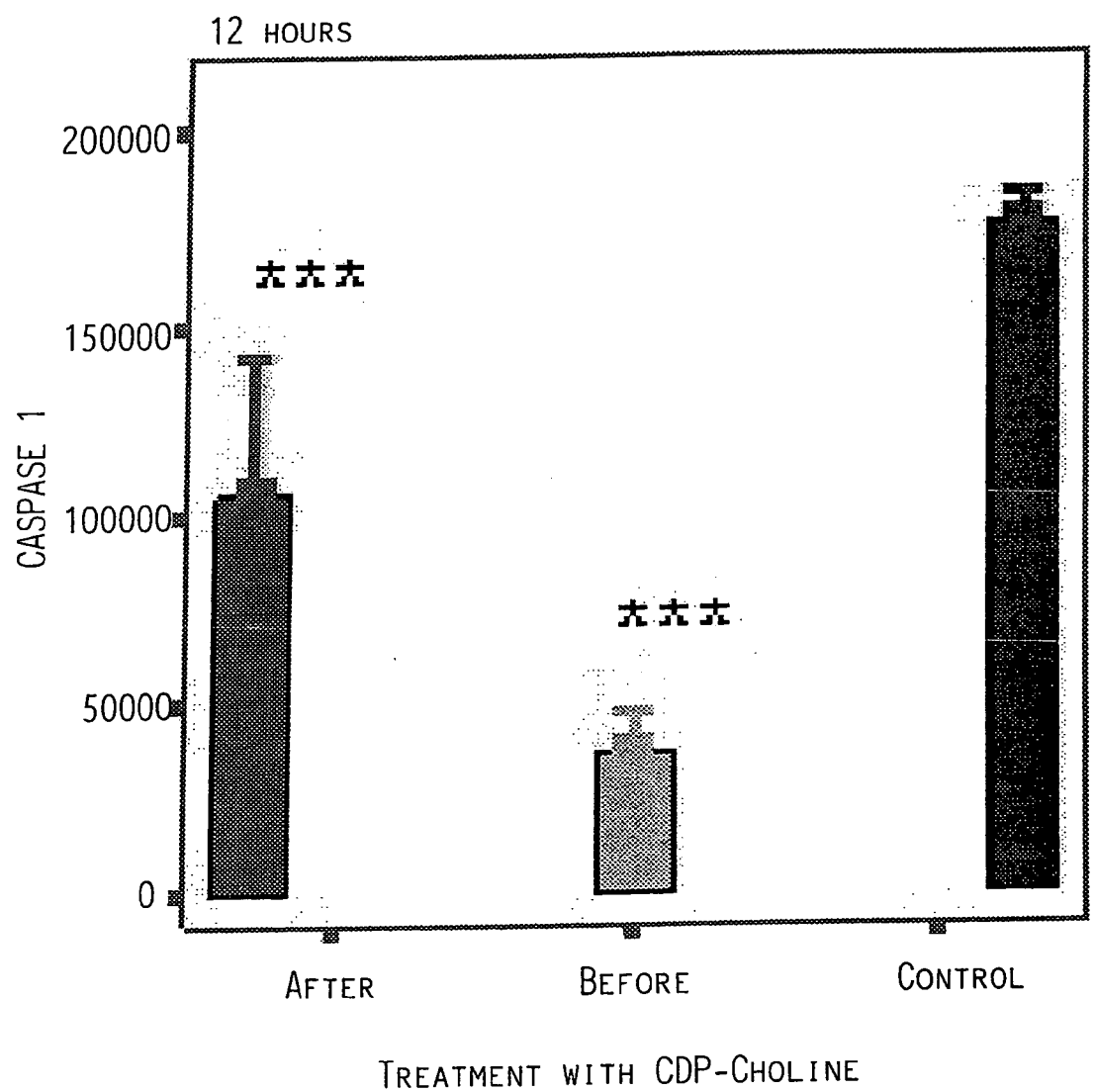
FIGS. 1, 2, 3, 4 and 5 depict bar graphs of mean values of measurement of caspases 1, 2, 3, 6 and 8, respectively, in immunofluorescence units. Confidence interval is 95% and statistical significance with respect to control is *p<0.05, p<0.025, *p<0.01.
Figure 2:
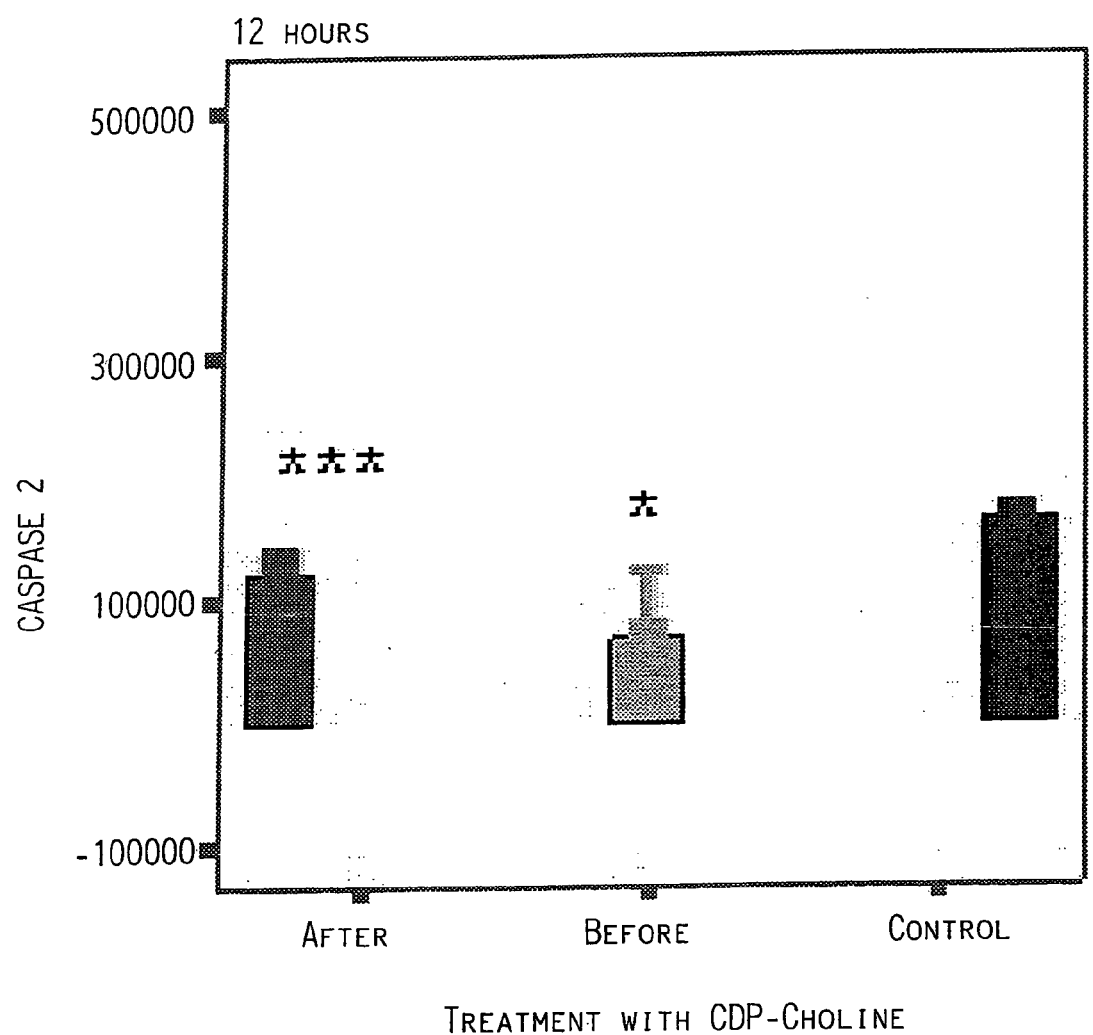
Figure 3:
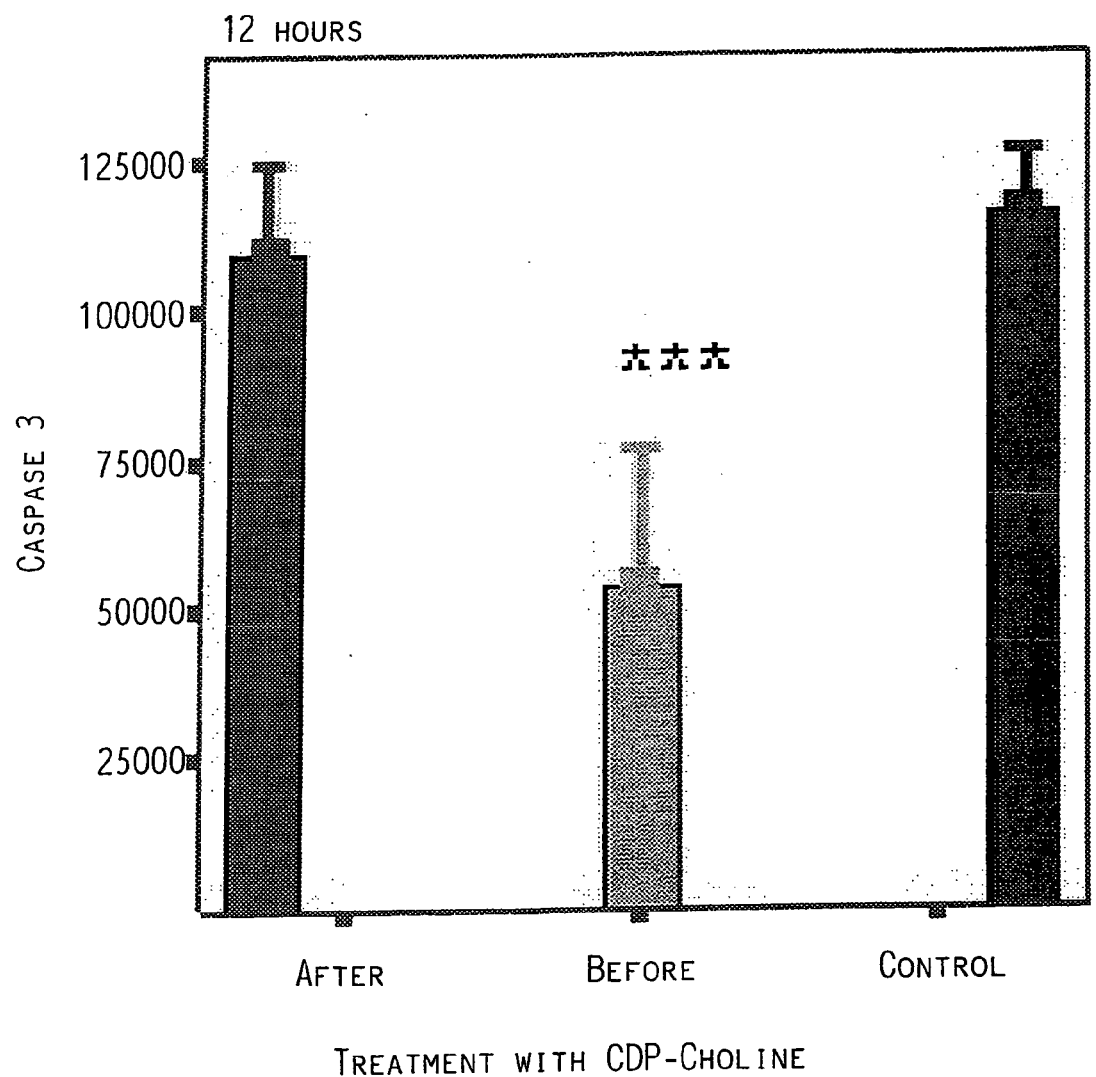
Figure 4:
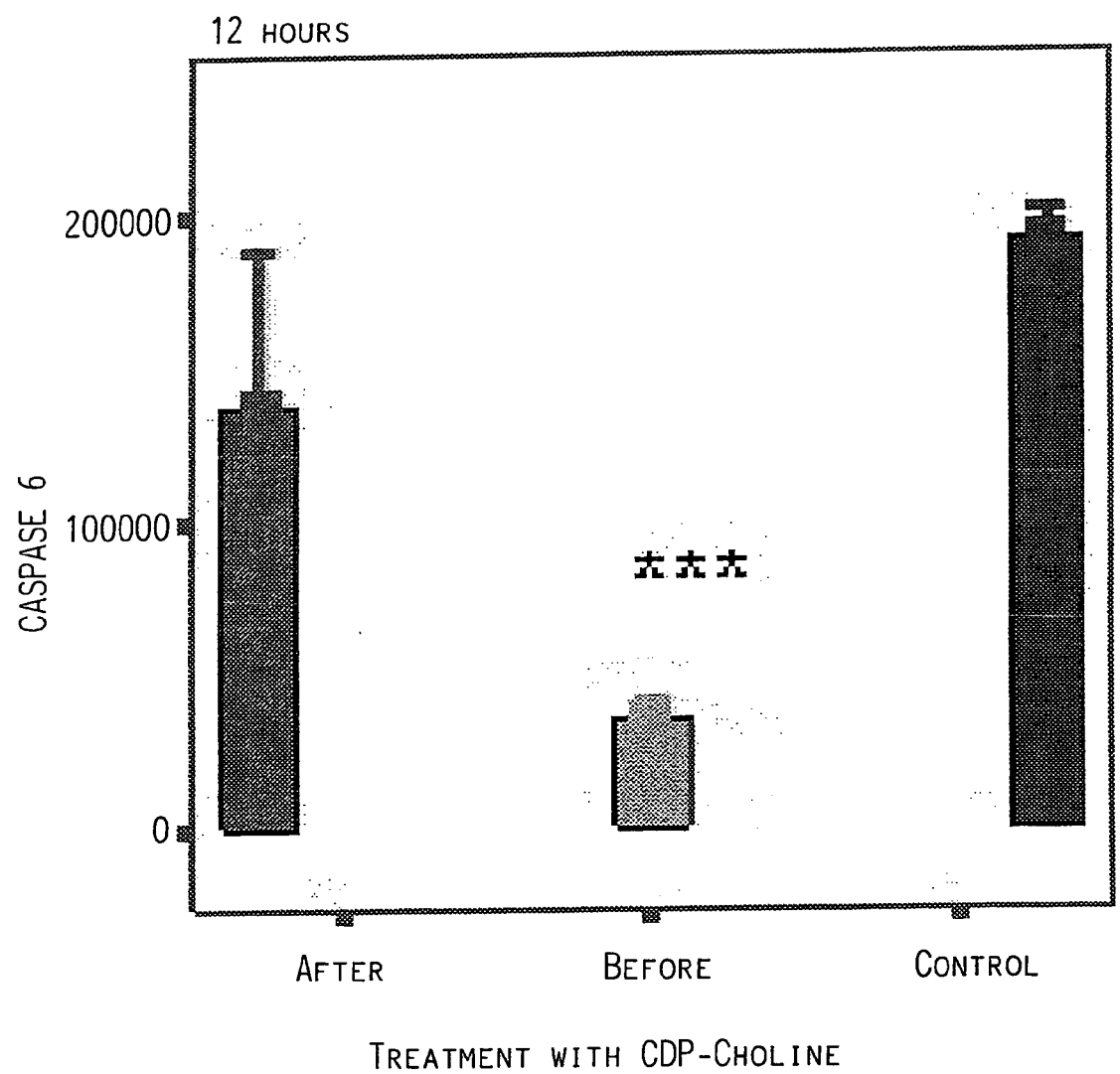
Figure 5:
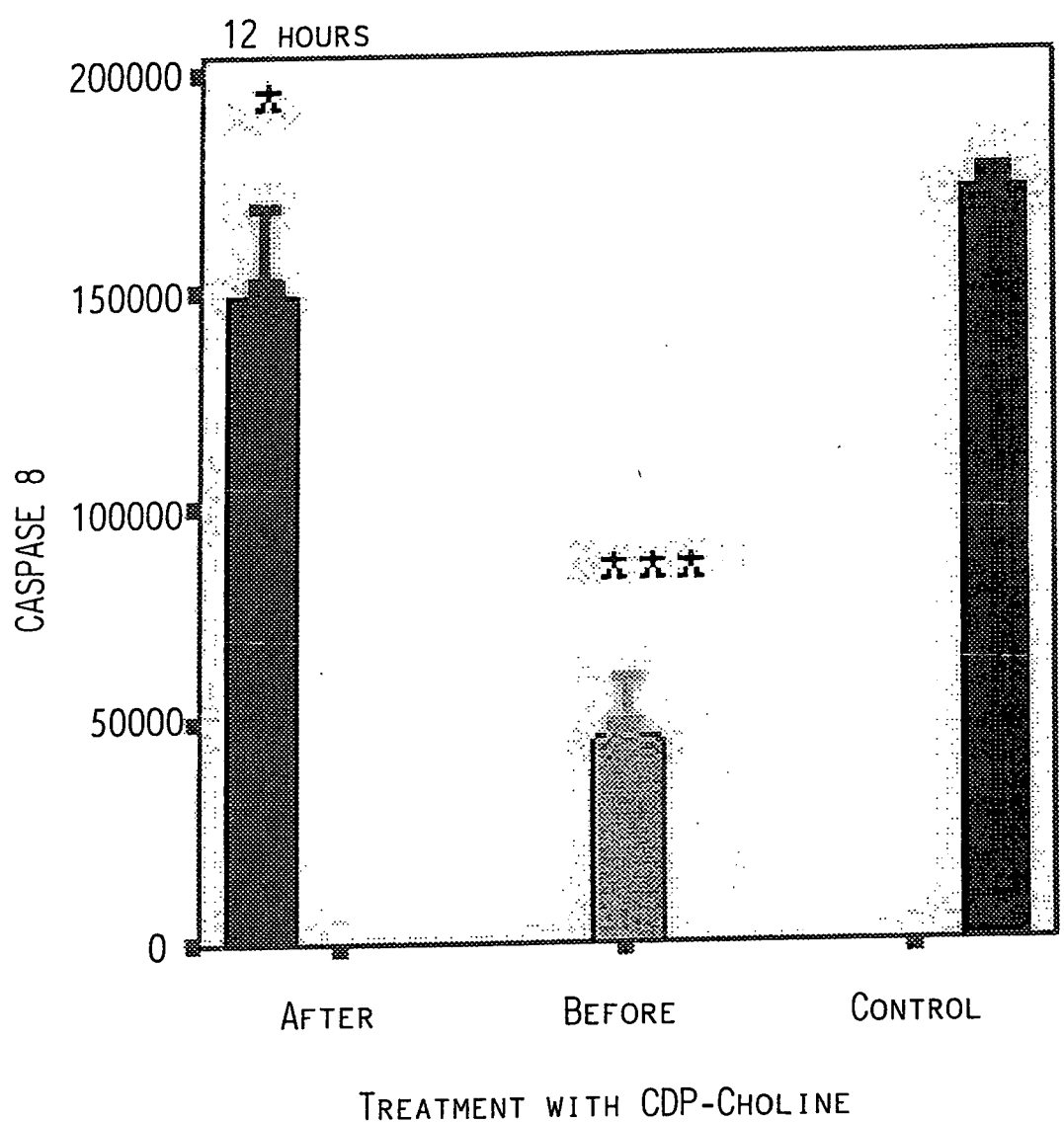

The invention claimed is:

1. A method for treating cerebral ischemia, comprising the step of administering an effective amount of CDP-Choline or a pharmaceutically acceptable salt thereof to a subject in need thereof prior to the onset of an ischemic episode, at daily doses in equivalent amounts of free CDP-Choline ranging from 1 gram to 2 grams,
wherein said subject in need thereof is one who is at high risk of suffering an acute ischemic event due to a known risk factor.

2. The method according to claim 1, wherein the pharmaceutically acceptable salt of CDP-Choline is an alkaline or alkaline earth salt or a salt with a mineral or organic acid, in anhydrous or hydrated form.

3. The method according to claim 1, wherein the pharmaceutically acceptable salt of CDP-Choline is selected from the group consisting of hydrochloric acid, hydrobromic acid, sulphuric acid, acetic acid, trifluoroacetic acid, citric acid, lactic acid, malonic acid, tartaric acid, acrylic acid, methacrylic acid, malic acid, maleic acid, fumaric acid, benzoic acid, salicylic acid, cinnamic acid, methane sulphonic acid, benzenesulphonic acid, p-toluenesulphonic acid, and nicotinic acid.

4. The method according to claim 1, wherein the acute ischemic event is a stroke.

5. The method according to claim 1, wherein the known risk factors are selected from the group consisting of a history of previous transient ischemic episodes, arterial hypertension, hypercholesterolemia, smoking, auricular fibrillation and embolic heart disease.

6. The method according to claim 1, wherein the subject is a human patient.

7. A method for protecting brain tissue from ischemic damage comprising administering to a subject in need thereof an effective amount of CDP-Choline or a pharmaceutically acceptable salt thereof prior to an onset of cerebral ischemic episode in said subject,
wherein said subject in need thereof is one who is at high risk of suffering an acute ischemic event due to known risk factors.

8. The method according to claim 7, wherein the pharmaceutically acceptable salt of CDP-Choline is an alkaline or alkaline earth salt or a salt with a mineral or organic acid, in anhydrous or hydrated form.

9. The method according to claim 7, wherein the pharmaceutically acceptable salt of CDP-Choline is selected from the group consisting of hydrochloric acid, hydrobromic acid, sulphuric acid, acetic acid, trifluoroacetic acid, citric acid, lactic acid, malonic acid, tartaric acid, acrylic acid, methacrylic acid, malic acid, maleic acid, fumaric acid, benzoic acid, salicylic acid, cinnamic acid, methane sulphonic acid, benzenesulphonic acid, p-toluenesulphonic acid, and nicotinic acid.

10. The method according to claim 7, wherein the acute ischemic event is a stroke.

11. The method according to claim 7, wherein the known risk factors are selected from the group consisting of a history of previous transient ischemic episodes, arterial hypertension, hypercholesterolemia, smoking, auricular fibrillation and embolic heart disease.

12. The method according to claim 7, wherein the subject is a human patient.

* * * * *